(12) United States Patent
Fish et al.

(10) Patent No.: US 11,322,261 B2
(45) Date of Patent: May 3, 2022

(54) SYSTEM AND METHOD FOR IMPLEMENTING AUGMENTED REALITY DURING TELEHEALTH SESSIONS IN A TELEHEALTH DEVICE

(71) Applicant: 19LABS INC., Menlo Park, CA (US)

(72) Inventors: Ram Adva Fish, Menlo Park, CA (US); Gerald Charles Horel, British Columbia (CA)

(73) Assignee: 19Labs Inc., Menlo Park, CA (US)

( * ) Notice: Subject to any disclaimer, the term of this patent is extended or adjusted under 35 U.S.C. 154(b) by 0 days.

(21) Appl. No.: 15/939,313

(22) Filed: Mar. 29, 2018

(65) Prior Publication Data

US 2018/0226158 A1 Aug. 9, 2018

Related U.S. Application Data

(63) Continuation-in-part of application No. 15/480,438, filed on Apr. 6, 2017, now abandoned.
(Continued)

(51) Int. Cl.
*G16H 80/00* (2018.01)
*A61B 5/00* (2006.01)
(Continued)

(52) U.S. Cl.
CPC .......... *G16H 80/00* (2018.01); *A61B 5/0022* (2013.01); *A61B 5/0024* (2013.01); *G16H 10/60* (2018.01); *G16H 30/20* (2018.01); *G16H 40/67* (2018.01)

(58) Field of Classification Search
None
See application file for complete search history.

(56) References Cited

U.S. PATENT DOCUMENTS

| 2007/0223574 A1* | 9/2007 | Roman | H04N 21/4854 375/240.01 |
|---|---|---|---|
| 2007/0299316 A1* | 12/2007 | Haslehurst | A61B 5/0002 600/300 |

(Continued)

FOREIGN PATENT DOCUMENTS

EP 0805600 A2 * 11/1997 ............. H04N 19/48

OTHER PUBLICATIONS

Multiplexing, Mar. 24, 2016, Wikipedia (Year: 2016).*
(Continued)

*Primary Examiner* — Christopher L Gilligan
*Assistant Examiner* — Karen A Hranek
(74) *Attorney, Agent, or Firm* — Inventive Law Inc.; Jim H. Salter

(57) ABSTRACT

A telehealth device includes a memory, a processor, one or more cameras, and a communication interface for relaying a data communication between a remote mobile device of a medical practitioner and the telehealth device used by a user over a communication network in a single communication channel. The processor may be configured to receive measurements of the user from one or more medical sensors, to collect medical information about the user, to overlay multiple layers of the collected medical in about the user including the received measurements over the data communication, to send the data communication over the communication network with the overlaid multiple layers for display on the remote mobile device of the medical practitioner, to execute commands sent from the remote mobile device in the single communication channel, so as to allow, based on the commands, the medical practitioner to remotely control the telehealth device.

20 Claims, 3 Drawing Sheets

Related U.S. Application Data

(60) Provisional application No. 62/320,190, filed on Apr. 8, 2016.

(51) Int. Cl.
  *G16H 40/67* (2018.01)
  *G16H 10/60* (2018.01)
  *G16H 30/20* (2018.01)

(56) References Cited

U.S. PATENT DOCUMENTS

| | | | | |
|---|---|---|---|---|
| 2010/0131280 A1* | 5/2010 | Bogineni | ................ | G08C 17/02 704/275 |
| 2011/0249075 A1* | 10/2011 | Abuan | .................. | G06F 3/0486 348/14.02 |
| 2013/0332616 A1* | 12/2013 | Landwehr | ............... | H04L 65/60 709/227 |
| 2014/0011477 A1* | 1/2014 | Shaikh | .................... | H04W 4/14 455/411 |
| 2014/0058755 A1* | 2/2014 | Macoviak | ............. | G06F 19/328 705/3 |
| 2015/0088546 A1* | 3/2015 | Balram | .................. | G16H 10/60 705/3 |
| 2015/0149201 A1* | 5/2015 | Starmer, Jr. | ............ | G16H 50/30 705/2 |
| 2015/0261930 A1* | 9/2015 | Espinosa Escalona | ...................... | A61B 5/0015 705/2 |
| 2016/0119553 A1* | 4/2016 | Alm | ..................... | G06K 9/3241 348/143 |
| 2017/0235905 A1* | 8/2017 | Santiago, Jr. | ....... | G06F 19/3418 705/2 |

OTHER PUBLICATIONS

Sachpazidis, Image and Medical Data Communication Protocols for Telemedicine and Teleradiology, Nov. 2008, Technical University of Darmstadt (Year: 2008).*

* cited by examiner

SYSTEM AND METHOD FOR IMPLEMENTING AUGMENTED REALITY DURING TELEHEALTH SESSIONS IN A TELEHEALTH DEVICE

RELATED APPLICATIONS

The present patent application is a continuation-in-part of U.S. patent application Ser. No. 15/480,438 filed on Apr. 6, 2017, which is incorporated herein by reference.

FIELD OF THE INVENTION

The present invention relates generally to a system and method for a telehealth device implementing augmented reality in communications with a remote mobile device over a communication network.

BACKGROUND OF THE INVENTION

In many cases, people may require medical assistance in remote locations or at locations without medical personnel. Typically, businesses and homeowners, for example, may have first aid kits available, based on the assumption that somebody at the location will have basic knowledge to use the contents of the first aid kit. However, unskilled lay people may be available at the location may have little or no knowledge for assisting the person in need of medical assistance. Likewise, the available people may not even know who to call for receiving help.

A telemedicine, or telehealth system, may be used to provide guidance to an available person for helping the patient in need of medical assistance. The telemedicine device may be configured to measure medical parameters of the person in need of medical assistance, such as from medical sensors attached to the patient's body, used for assessing the state of the person and relay that information to one or more remote practitioners, such as a doctor. For the remote practitioners to assess the patient's medical state, they may need the medical history of the patient, to act feedback from other persons knowledgeable about the patient's state, such as parents, for example, if the patient is a child, and to see and/or communicate with the patient. Thus, the remote practitioner may need to use and/or access multiple different computer systems, databases and applications, which may result in cost and security challenges.

Thus, it may be desirable to have a telehealth device configured to receive medical information from the patient, from other persons with knowledge of the patient's medical state, and from multiple databases. The telehealth device may then process, organize, and present the medical information from the different sources efficiently for a remote practitioner to view on a remote computerized device, so as to assess the medical state of the patient. The telehealth device may also allow the remote practitioner to control the remote diagnostic biosensor devices and to relay instructions to the patient.

Embodiments of the present invention herein describe a system and method for implementing augmented reality during telehealth sessions in a telehealth device for presenting and relaying medical information of a patient or user to a medical practitioner on a remote computerized device, such as a remote mobile device. The system may further include a telehealth device (e.g., a tablet computer) with various connectable medical sensors for evaluating a patient's status and/or treating the patient. The system may include an application that allows the patient and/or a user assisting the patient to communicate with one or more remote medical practitioners by using voice, video technology, or both via a connected device of the remote medical practitioner, such as, for example, a personal computer, a tablet, or a remote mobile device.

A voice call and/or a video call may be placed by the patient and/or by the user assisting the patient to one or more remote medical practitioners via the telehealth device. The voice call and/or video call may be further augmented by allowing the one or more remote medical practitioners to control the application operating on the telehealth device and associated devices with either voice commands, text commands, or both. These commands may include displaying instructions on how to deploy for example, one or more medical sensors coupled to the telehealth device for examining the patient, to display measurement information from the one or more medical sensors, and to control any devices including the one or more medical sensors coupled to the telehealth device.

In some embodiments of the present invention described herein, the telehealth device may receive medical information from the patient (e.g., from the one or more medical sensors), from other persons with knowledge of the patient's medical state, and from multiple databases with the patient's private details, medical history, and another other relevant medical information. The telehealth device, in turn, may apply augment reality schemes to the video, voice, and/or messaging channel between the patient and the one or more remote practitioners with real time information about the patient. The telehealth device may then process, organize, and present the medical information efficiently for a remote practitioner to view on a remote computerized device, such as a remote mobile device, so as to assess the medical state of the patient. For example, the telehealth device may overlay measurements, patient data, and a video of the patient in one video display, such as the sensor measurements, patient's name, patient's location, and any other suitable data. Thus, the embodiments provided herein preclude the need for the medical practitioner to use any other system or to toggle between different systems to retrieve patient information.

There is thus provided, in accordance with some embodiments of the present invention, a telehealth device including a memory, a processor, one or more cameras and a communication interface for relaying a data communication between a remote mobile device of a medical practitioner and the telehealth device used by a user over a communication network in a single communication channel. The one or more cameras may be used for capturing an image of the user for the data communication. The processor may be configured to establish the data communication, to receive measurements of the user from one or more medical sensors, to collect medical information about the user from one or more databases, to overlay multiple layers of the collected medical information about the user including the received measurements over the data communication, to send the data communication over the communication network with the overlaid multiple layers to the remote mobile device of the medical practitioner, to execute commands sent from the remote mobile device in the single communication channel, so as to allow, based on the commands, the medical practitioner to remotely control the telehealth device.

Furthermore, in accordance with some embodiments of the present invention, the user may include a patient.

Furthermore, in accordance with some embodiments of the present invention, the image may include a live video or a still image captured by the one or more cameras.

Furthermore, in accordance with some embodiments of the present invention, the data communication may be selected from the group consisting of a video call, a text message, chat, and a phone call.

Furthermore, in accordance with some embodiments of the present invention, the collected medical information may be selected from the group consisting of a patient name, a patient medical history, and the received measurements.

Furthermore, in accordance with some embodiments of the present invention, the processor may be configured to collect medical information of the user from the one or more databases from the memory, or from one or more remote computing devices communicating over the communication network.

Furthermore, in accordance with some embodiments of the present invention, the processor may be configured to execute the commands sent from the remote mobile device by voice or text messages in the data communication.

Furthermore, in accordance with some embodiments of the present invention, the processor may be configured to execute the commands by parsing a text message sent from the remote mobile device in the data communication and identifying the commands from keywords in the text message.

Furthermore, in accordance with some embodiments of the present invention, the processor is configured to execute the commands by deciphering a data stream from a voice message sent from the remote mobile device in the data communication and applying voice recognition to the data stream to identify the command.

Furthermore, in accordance with some embodiments of the present invention, the data communication may include a voice or chat message, and the processor may be configured to send the collected medical information about the user to the remote mobile device in the voice or the chat message in response to the command.

There is further provided, in accordance with some embodiments of the present invention, a method including in a processor of a telehealth device, establishing a data communication between a remote mobile device of a medical practitioner and the telehealth device used by a user over a communication network, in a single communication channel. Measurements may be received from one or more medical sensors of a user of the telehealth device. Medical information about the user may be collected from one or more databases. Multiple layers of the collected medical information about the user including the received measurements may be overlaid over the data communication. The data communication may be sent over the communication network with the overlaid multiple layers to the remote mobile device of the medical practitioner. Commands sent from the remote mobile device in the single communication channel may be executed, so as to allow, based on the commands, the medical practitioner to remotely control the telehealth device.

BRIEF DESCRIPTION OF THE DRAWINGS

The embodiments of the present invention will be understood and better appreciated from the following detailed description taken in conjunction with the drawings. Identical structures, elements or parts, which appear in more than one figure, are generally labeled with the same or similar number in all the figures in which they appear, wherein.

DETAILED DESCRIPTION

Figure 1:
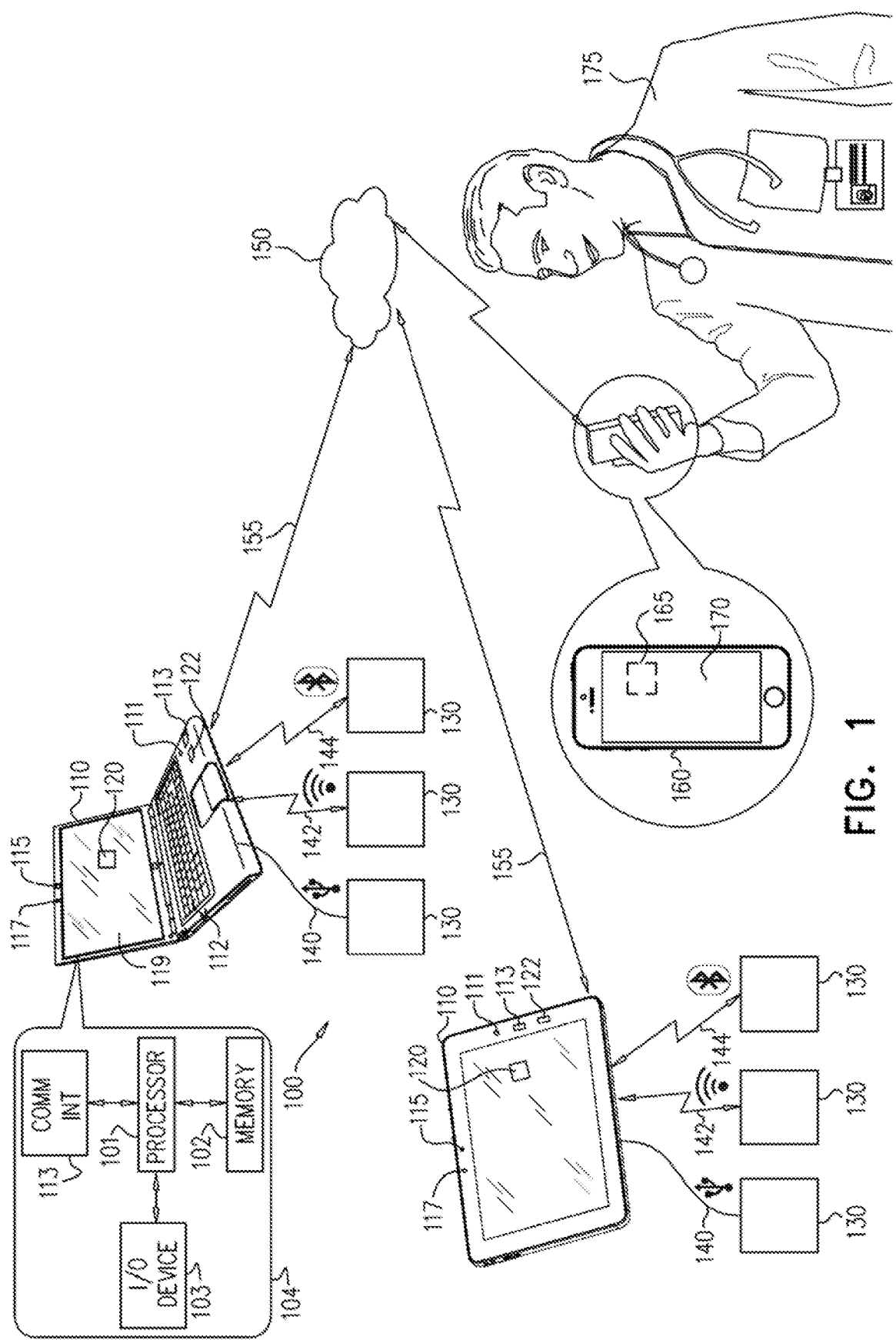
FIG. 1 schematically illustrates a telehealth system for receiving remote assistance from a medical practitioner, in accordance with some embodiments of the present invention.

FIG. 1 schematically illustrates a telehealth system 100 for receiving remote assistance from a medical practitioner 175, in accordance with some embodiments of the present invention. A user of telehealth system 100 may communicate with medical practitioner 175 using a telehealth device 110, may receive instructions from medical practitioner 175 via telehealth device 110, or may allow medical practitioner 175 to remotely control activities in telehealth system 100. Medical practitioner 175 may be equipped with a remote mobile device 160, for example a smartphone, tablet or other mobile communication device.

The term "user" of telehealth system 100 in this disclosure may refer to a patient or person needing medical assistance, or any person assisting the patient. Similarly, the term "medical practitioner" or "remote practitioner" may herein refer to a doctor, nurse, or any suitable person assisting the user from a remote location. Medical practitioner 175 may use telehealth device 100 to obtain medical information about the user, or about the patient if the user may be assisting the patient requiring medical assistance. Although FIG. 1 illustrates one medical practitioner 175 assisting the user using telehealth system 100, any suitable number of medical practitioners (e.g., one or more medical practitioners) may assist the user via telehealth system 100, each respectively accessing and/or controlling telehealth device 110 using a remote computing device.

In some embodiments of the present invention, telehealth device 110 may be implemented as a general-purpose computer. Telehealth device 110 may be provided as a desktop computer, a laptop computer (e.g., as shown in FIG. 1), a tablet computer (e.g., as shown in FIG. 1), a smartphone or other type of computational device. Telehealth device 110 may further include, as shown in an inset 104, a processor 101, a memory 102, input and/or output devices 103, and a communication interface 113.

In some embodiments of the present invention, a medical assistance application 120 may be stored in memory 102 and executed by processor 101 of telehealth device 110. Medical assistance application 120 may provide instructions to a patient or any user assisting the patient, receive measurements from medical sensors 130, send information to the medical practitioner 175, receive instructions from medical practitioner 175 and/or be controlled remotely by medical practitioner 175.

In some embodiments of the present invention, telehealth device 110 may include I/O devices 103 as well as other peripheral devices and communication units coupled to processor 101, such as a display 119, a front camera 115, a rear camera (not shown), a microphone 117, a keyboard 112, global positioning system (GPS) unit 111, and speakers 122. The display 119 may provide pictures and information to the user. Front camera 115 and microphone 117 allow medical practitioner 175 to see and/or hear the user and/or the patient on a remote mobile device 160. The different cameras on telehealth unit 110 may behave as a virtual camera. The virtual camera may be used to image the user for use in the video calls for medical practitioner 175 to view on display 170.

In some embodiments of the present invention, telehealth device 110 may include a communication interface 113 for communicating 155 a data communication with remote mobile devices 160 of one or more remote users (e.g., such as medical practitioner 175 shown in FIG. 1) over a network 150 (e.g., the internet, a cellular network, and/or a satellite network). Stated differently, processor 101 of telehealth device 110 may establish, relay, and/or maintain a data communication, such as a video call, voice call, chat, and/or text message, in a telehealth session with one or more remote computing devices, such as remote mobile device 140.

In some embodiments of the present invention, remote mobile device 160 may use an application 165 dedicated for communicating 155 with medical assistance application 120 on telehealth device 110. Alternatively, medical assistance application 120 may send remote mobile device 160 a link to a web that may be executed by a standard web browser.

In some embodiments of the present invention, remote mobile device 160 may include a display 170 for viewing information transmitted by telehealth device 110. The transmitted information may be, for example, a video of the patient augmented for example with overlaid video, voice, or text. Upon receiving a notification from the user, for example, medical practitioner 175 may connect to telehealth device 110 via a dedicated application 165, via a standard browser, or via other standard communication programs, such as SMS, MMS Video calls, Zoom, WhatsApp or similar applications for transmitting text, voice, pictures and/or video data.

In some embodiments of the present invention, processor 101 may be configured to collect information from other telehealth device 110 such as tablets or cellular devices used by users related to the patient, but may not be physically next to the patient. For example, if the patient is a child, remote medical practitioner 175 may need medical information about the child from the child's parents, guardians, and/or siblings. Remote medical practitioner 175 may send a request via text, chat or video to telehealth device 110 to instruct telehealth device 110 to contact these persons physically remote from the patient for information.

Additionally or alternatively, remote medical practitioner 175 may send a request to telehealth device 110 to contact other doctors (e.g., one or more additional medical practitioners), nurses, and any other suitable health care professionals to assist remote medical practitioner 175 in assessing the condition of the patient. Processor 101 in telehealth device 110 may collect personal and medical information about the patient from a database such as the medical history, contact persons related to the patient, personal details, and/or medications that the person may be using.

In some embodiments of the present invention, processor 101 may be configured (e.g., by executing medical assistance application 120, for example) to organize and prepare the collected medical information of the patient to be displayed on display 170 of remote mobile device 160 of remote medical practitioner 175. Processor 101 may organize and prepare the collected medical information to be visually overlaid and relayed over network 150 in a single video channel for display on display 170 of remote mobile device 160 of medical practitioner 175.

In some embodiments of the present invention, processor 101 may implement augmented reality and/or computer-mediated reality algorithms to organize and present the data to the medical practitioner on display 170. In this manner, this overlay feature of the collected information on display 170 may preclude the need for using and/or installing an additional application on remote mobile device 160 to manage the collected medical information, such that any standard application on remote mobile device 160 may be used.

In some embodiments of the present invention, medical sensors 130 may be connectable to telehealth device 110 via a USB connection 140, a local Wi-Fi connection 142, a Blue-Tooth connection 144 or other type of local connection. Optionally, medical assistance application 120 may configured to control the medical sensors 130, for example, to turn them on or off, receive results directly from the sensor in response to commands sent from the remote mobile device e.g., to repeat measurements or continue measuring responsive to a result). In some embodiments of the present invention, the sensors may be physically connected to the telehealth device 110 or physically independent. Medical assistance application 120 may be controlled by voice and/or text commands by medical practitioner 175 via remote mobile device 160.

In some embodiments of the present invention, medical sensors 130 may be coupled to telehealth device 110 for measuring medical information from a patient (e.g., user). The medical information from medical sensors 130 may be sent in one or more layers to be overlaid in the video displayed on display 170 of remote mobile device 160. For example, medical sensors 130 may include:
  1. A pulse oximeter to monitor a person's oxygen saturation ($SO_2$);
  2. A blood pressure sensor to measure a person's blood pressure;
  3. A stethoscope to listen to or record a person's lungs and/or heart or other internal sounds;
  4. An otoscope or similar device to view a person's ears or mouth;
  5. A thermometer;
  6. Other medical sensors.

In some embodiments of the present invention, medical assistance application 120 may display to the user a list of options. The list may include the option to call emergency medical assistance (e.g., 911) or a medical practitioner 175 (e.g., a practitioner on call) to receive assistance in using telehealth system 100, for example how to handle a specific situation and/or how to use a specific sensor.

In some embodiments of the present invention, the medical practitioner 175 is able to view the patient (e.g. via camera 115), hear the patient (e.g. via microphone 117) and/or provide verbal instructions and/or execute actions remotely via medical assistance application 120, which may be used to control telehealth device 110. For example, the practitioner may instruct the local user to deploy a specific sensor on the patient to measure vital signs of the patient. If permitted by the user (e.g., telehealth device 110 may allow the user to approve the relaying of the user's private details to the medical practitioner), medical practitioner 175 may view the results and provide further instructions. In other embodiments, medical practitioner 175 may remotely control medical assistance application 120 on telehealth device 110 via remote mobile device 160 by saying a command keyword into a microphone on remote mobile device 160 while talking to the patient, or by texting a command keyword while typing text messages to the patient.

In some embodiments of the present invention, medical practitioner 175 may issue command keywords via remote mobile device 160 such as:

1. "Display XXXX Guides"—Instructs medical assistance application 120 to display on display 119 local information or a guide to the user on telehealth device 110 about any medical condition generically denoted as XXXX. XXXX guide may refer to any guide on medical condition XXXX, such as a guide on croup, for example. The guides may be stored, for example, in a database in memory 102 on telehealth device 110. Alternatively or additionally, the guides may be stored in a database remote from telehealth device 110 and relayed to telehealth device 110 via network 150;
2. "Patient Info"—Instructs medical assistance application 120 to relay information about the patient from telehealth device 110 to remote mobile device 160. The patient information (e.g., name and location of the patient) may be overlaid on the video of patient on display 170, may be sent as a text message to remote mobile device 160, or may be sent as speech data to be played on a speaker on remote mobile device 160 and heard by medical practitioner 175;
3. "Display Help"—Instructs medical assistance application 120 to relay information from telehealth device 110 to remote mobile device 160 about the basic commands that medical assistance application 120 supports. The information may be overlaid over the video of patient on display 170, by sending the information as a text message to remote mobile device 160, or by sending the information as speech data to be played on a speaker on remote mobile device 160 and heard by medical practitioner 175;
4. "Select Sensor XXXX"—Instructs medical assistance application 120 to activate a specific medical sensor, where XXXX denotes the type of medical sensor 130, and to relay the information measured by the designated medical sensor back to remote mobile device 160 for medical practitioner 175. The information measured by the designated medical sensor may be overlaid on display 130 over the video, voice, or chat application;
5. "Call Help"—Instructs medical assistance application 120 on telehealth device 110 to initiate communication with a designated emergency contact such as phone call to 911 emergency services, for example. In some embodiments, the emergency call may be initiated remotely on telehealth device 110 by medical practitioner 175 on remote mobile device 160;
6. "Activate Application XXXX" Instructs medical assistance application 120 on telehealth device 110 to activate a specific service or application denoted XXXX that may be resident on medical assistance application 120 (e.g., electrocardiogram ECG device dedicated application). Medical assistance application 120 may overlay the service or application on display 170 or a video of the patient, or may display the service or application on display 170 instead of the patient video.

Figure 2:
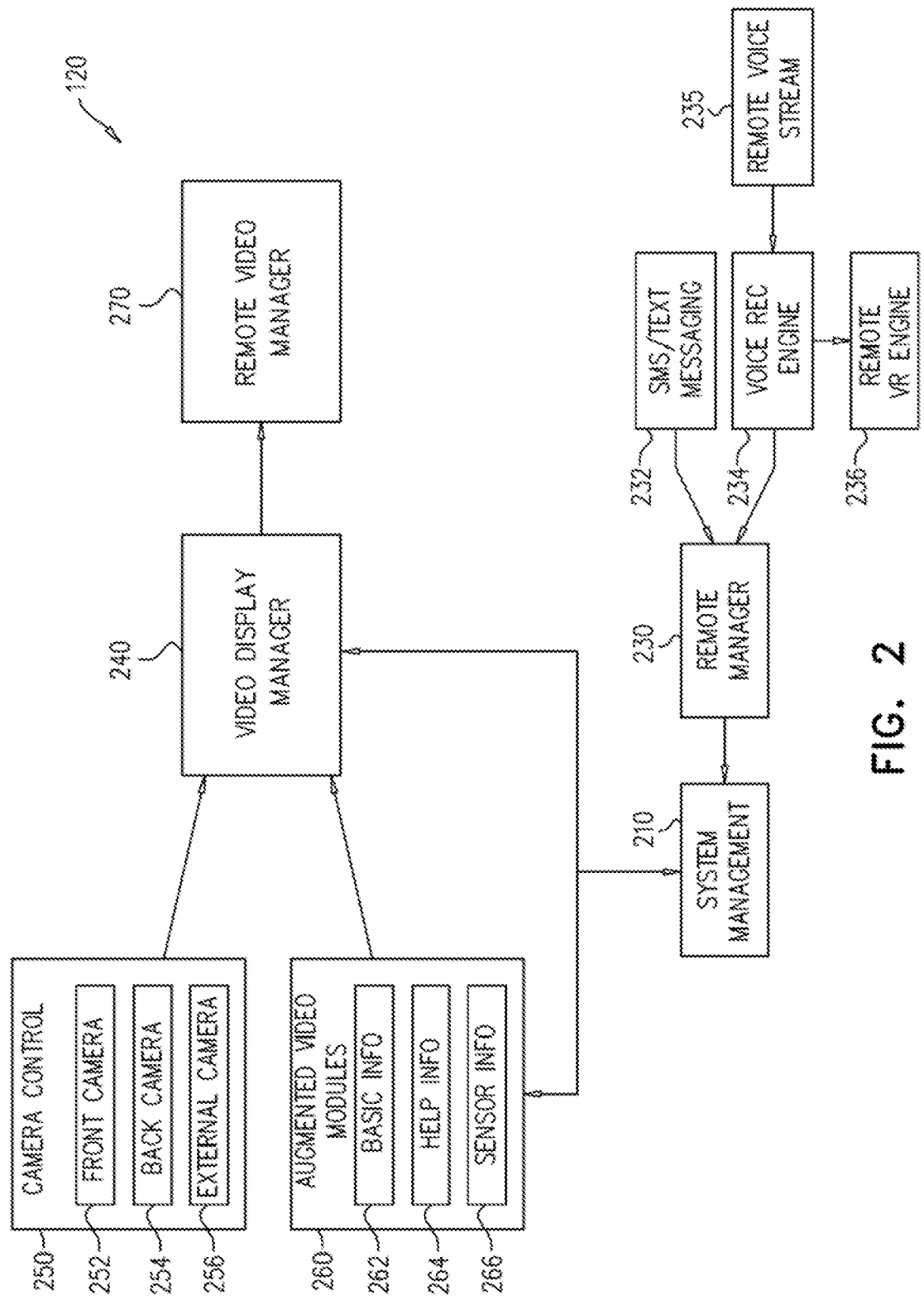
FIG. 2 is a schematic block diagram of elements of a medical assistance application for communicating with a medical practitioner, in accordance with some embodiments of the present invention.

FIG. 2 is a schematic block diagram of medical assistance application 120 for communicating with remote mobile device 160, in accordance with some embodiments of the present invention. Remote mobile device 160 may receive a voice communication spoken by medical practitioner 175, which may be subsequently relayed to medical assistance application 120 (e.g., processor 101) running on telehealth device 110 via network 150 as a data stream of voice information (e.g., remote voice stream 235). Additionally or alternatively, remote mobile device 160 may receive data from text messages from medical practitioner 175, which may be subsequently relayed to medical assistance application 120 running on telehealth device 110 via network 150.

In some embodiments of the present invention, a remote manager 230 receives the voice and/or text message data from remote mobile device 160, parses the information and takes appropriate actions based on the request and/or commands extracted from text and/or voice messages from medical practitioner 175 using remote mobile device 160. In some embodiments, the voice and/or text message data may be received and processed by various modules of medical assistance application 120 such as:

1. A text/SMS messaging unit 232 that receives text information and commands from remote mobile device 160;
2. A voice recognition engine 234 that receives the data stream from voice messages from remote voice stream 235 and deciphers the voice messages so that medical assistance application 120 can act on the information. Voice recognition engine 234 may be configured to identify keywords and command keywords in the data stream. Optionally, voice recognition engine 234 may send audio information to a remote voice recognition engine 236 to help process the data stream, so as to decipher audio commands.

In some embodiments of the present invention, remote manager 230 may parse and analyze the identified text commands (e.g., "Call 911") from SMS/Text messaging unit 232 and/or voice commands from Voice Recognition engine 234. Remote manager 230 may check the validity of the text/voice commands. Remote manager 230 may translate them to appropriate respective system commands for execution by processor 101 in telehealth device 110. For example, medical practitioner 175 may issue a voice/text comment such as "Call 911". Remote manager 230 may translate "Call 911" to a command "Place Phone Call to Telephone Number=911" executed by processor 101. Remote manager 230 may convert the command from processor 101 to the appropriate application programming interface (API) calls, such as terminating the existing communication, starting the phone call to 911, and changing display 119 to "Calling 911".

In some embodiments of the present invention, medical assistance application 120 may include a system management routine 210 that may be installed on telehealth device 110. In other embodiments, system management routine 210 may control actions between telehealth device 110 and a remote manager 230. Remote manager 230 may control actions of remote mobile device 160 that is communicating with the medical assistance application 120.

In some embodiments of the present invention, medical assistance application 120 may include an augmented video module 260, and a camera control module 250 that may control the reception of images from one or more cameras connected to telehealth device 110. Camera control module 250 may include a front camera control module 252, a rear camera control module 254, an external camera module 256 (e.g. connected to telehealth device 110 via USB). Camera control module 250 may collect visual information and provide images to a video display manager 240, which may combine the video selected channel, such as front camera 252, for example, with visual elements created by an augmented video module 260 for display to medical practitioner 175 on display 165. Video display manager 240 may also augment the voice or text channel by injecting the information into them.

In some embodiments of the present invention, augmented video module 260 may include a basic information menu 262, a help information menu 264 and a sensor information menu 266 for display on remote mobile device 160 to assist medical practitioner 175. These modules may use the information from telehealth device 110 and prepare it as visual information to be overlaid in multiple layers over the video channel. In some embodiments, basic information menu 262 may display details about the patient information and location for overlay on a video channel displayed on display 170. Help menu 264 may display help screens on display 170 help screens system commands recognized remote manager 230 overlaid on the video. Sensor information module 266 may convert the measurement readings from medical sensors 130 into visual information on display 170. Sensor information module 266 may allow medical practitioner 175 to control use of the sensors, to set configuration parameters for the sensors, and to view results from medical sensors 130 for transfer to video display manager 240 for display on remote mobile device 160.

In some embodiments of the present invention, video display manager 240 may receive and prepare information for display on remote mobile device 160. Optionally, some of the information may be transferred to a remote video manager 270 that prepares the information and images for transmission via network 150 to the remote practitioner 175 for display on display 170 of remote mobile device 160.

Figure 3:
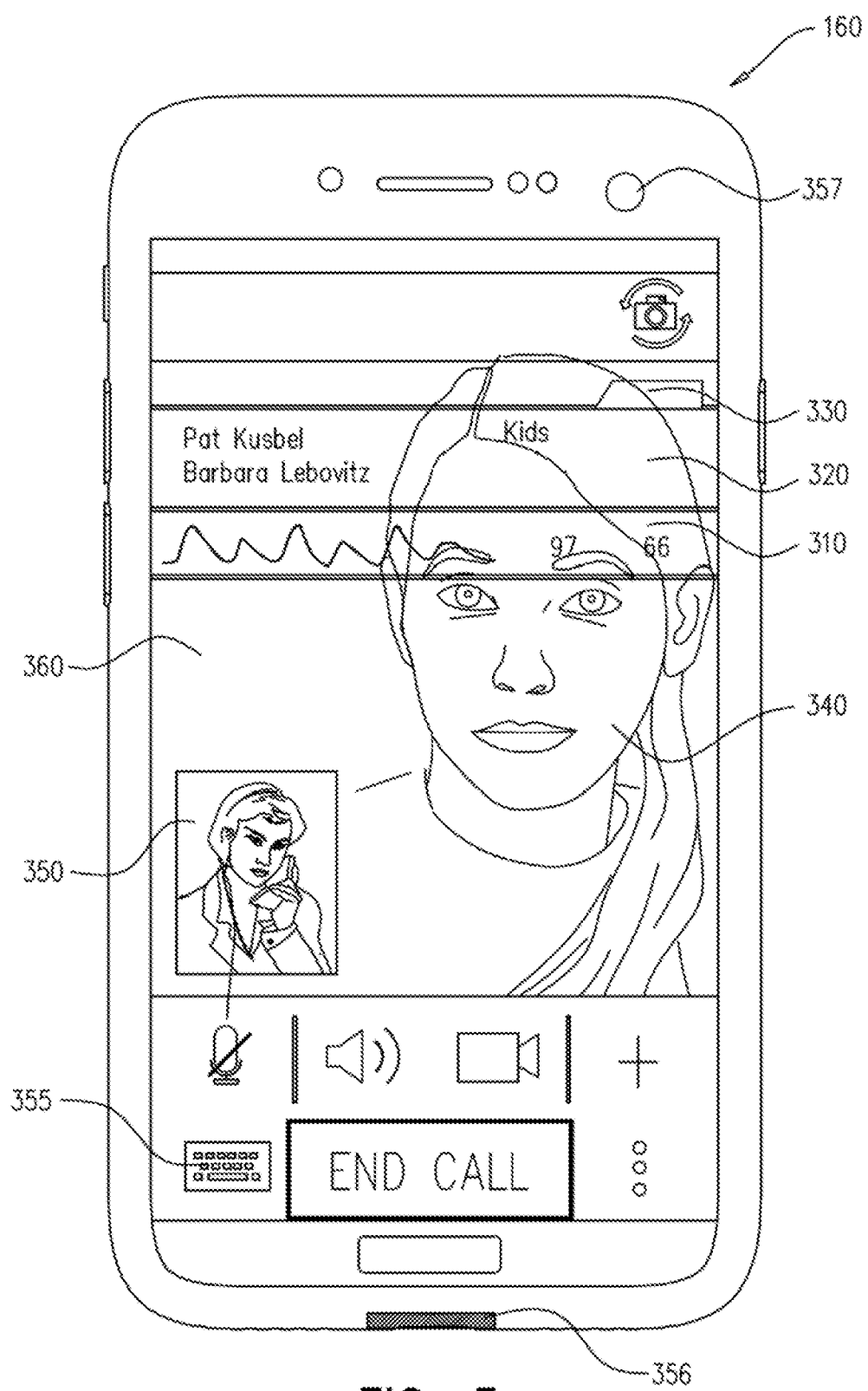
FIG. 3 schematically illustrates an exemplary display of a remote mobile device augmented with multiple layers of information, in accordance with some embodiments of the present invention.

FIG. 3 schematically illustrates an exemplary display 360 on remote mobile device 160 augmented with multiple layers of information, in accordance with some embodiments of the present invention. Remote mobile device 160 may include display 360, a keyboard 355, a speaker/microphone unit 356 and a front camera 357 for capturing still images and/or videos of medical practitioner 175.

Display 360 may display a video call between a patient 340 and medical practitioner 175. Video display manager 240 on medical assistance application 120 on telehealth device 110 may overlay the patient video from front camera module 252 with basic patient information received by basic information module 262 from a database on telehealth device 110. The database may be stored in memory 102 on telehealth device 110. Alternatively or additionally, the patient data may be stored on any suitable storage device in any remote location and uploaded to telehealth device 110 via network 150.

In some embodiments of the present invention, remote video manager 270 may prepare a single channel of video prepared by using data collected from camera control module 250 and augmented video modules 260. Remote video manager 270 may overlay the following information in multiple layers, which may be transmitted to remote mobile device 160 for display on display 360, which may include:

1. A live image or still image of patient 340 from images sent by medical assistance application 120 (e.g. the user of telehealth device 110) captured by the cameras;
2. One or more tabs 330 to activate command menus or help menus that may be selected by medical practitioner 175 during the telehealth session;
3. A basic overlay text 320 providing basic patient info information, for example, such as the identity of the user that communicated, duration of the call, as well as names and contact details of health care providers, kids, and any other suitable details related to patient 340 using telehealth device 110. For example, basic information module 262 may convert the patient information and location that may be converted to basic overlay text 320 on video on display 360. Alternatively or additionally, voice information or text information such as, for example, "Patient is Pat Kusbel and is at home in Menlo Park" may be displayed as text on display 360 or audibly output from speaker 356;
4. Sensor reading bar 310 that provides sensor readings from medical sensors 130 for the view by medical practitioner 175, such as an exemplary ECG reading as shown in FIG. 3. Sensor information module 266 converts the medical sensor elements into visual information as viewed as an ECG reading for example on sensor reading bar 310, overlaid over the video;
5. A practitioner icon 350 showing a symbol of medical practitioner 175 that is displayed to the user on display 119 of telehealth device 110.

In some embodiments of the present invention, remote video manager 270 may overlay different layers of collected medical information over the data communication (e.g., video call) for display on display 360 to the medical practitioner as shown in the exemplary embodiment of FIG. 3. Overlaying the different layers of collected medical information over the video in this manner may reduce the need for the medical practitioner to toggle between different sources of medical information regarding the patient such as, for example, different persons on video calls, voice calls, or chat applications as well as different databases. Thus, the medical practitioner 175 may obtain the necessary medical information for efficiently diagnosing the medical problem of the patient, and for quickly deciding what medical procedures and/or medications may be needed by the patient.

In some embodiments of the present invention, medical practitioner 175 may talk to the patient on a telephone call using remote mobile device 160. The data may be sent from telehealth device 110 and may be viewed by medical practitioner 175 as a text message without any video displayed. Conversely, medical practitioner 175 may send text information to the patient as text messaging. Additionally, medical practitioner 175 may send commands to control telehealth device 110 as text commands using a text messaging application, for example, on remote mobile device 160.

In some embodiments of the present invention, a telehealth device may include a memory, a processor, one or more cameras, and a communication interface for relaying a data communication between a remote mobile device of a medical practitioner and the telehealth device used by a user over a communication network in a single communication channel. The one or more cameras may be used for capturing an image of the user for the data communication. The processor may be configured to establish the data communication, to receive measurements of the user from one or more medical sensors, to collect medical information about the user from one or more databases, to overlay multiple layers of the collected medical information about the user including the received measurements over the data communication, to send the data communication over the communication network with the overlaid multiple layers (e.g., for display on) to the remote mobile device of the medical practitioner, to execute commands sent from the remote mobile device in the single communication channel, so as to allow, based on the commands, the medical practitioner to remotely control the telehealth device.

In some embodiments of the present invention, the user may include a patient.

In some embodiments of the present invention, the image may include a live video or a still image captured by the one or more cameras.

In some embodiments of the present invention, the data communication may be selected from the group consisting of a video call, a text message, chat, and a phone call.

In some embodiments of the present invention, the collected medical information may be selected from the group consisting of a patient name, a patient medical history, and the received measurements.

In some embodiments of the present invention, the processor may be configured to collect medical information of the user from the one or more databases from the memory, or from one or more remote computing devices communicating over the communication network.

In some embodiments of the present invention, the processor may be configured to execute the commands sent from the remote mobile device by voice or text messages in the data communication.

In some embodiments of the present invention, the processor may be configured to execute the commands by parsing a text message sent from the remote mobile device in the data communication and identifying the commands from keywords in the text message.

In some embodiments of the present invention, the processor is configured to execute the commands by deciphering a data stream from a voice message sent from the remote mobile device in the data communication and applying voice recognition to the data stream to identify the command.

In some embodiments of the present invention, the data communication may include a voice or chat message, and the processor may be configured to send the collected medical information about the user to the remote mobile device voice or the chat message in response to the command.

In some embodiments of the present invention, a method may include in a processor of a telehealth device, establishing a data communication between a remote mobile device of a medical practitioner and the telehealth device used by a user over a communication network in a single communication channel. Measurements may be received from one or more medical sensors of a user of the telehealth device. Medical information about the user may be collected from one or more databases. Multiple layers of the collected medical information about the user including the received measurements may be overlaid over the data communication. The data communication may be sent over the communication network with the overlaid multiple layers to the remote mobile device of the medical practitioner. Commands sent from the remote mobile device in the single communication channel may be executed, so as to allow, based on the commands, the medical practitioner to remotely control the telehealth device.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the present invention. Further combinations of the above features are also considered to be within the scope of some embodiments of the present invention.

It will be appreciated by persons skilled in the art that the present invention is not limited to what has been particularly shown and described hereinabove. Rather the scope of the present invention is defined only by the claims, which follow.

The invention claimed is:

1. A method for remotely treating a patient using a patient telehealth device configured to send both patient video and patient information through a single combined video stream over a communication network to a remote clinician device, the method comprising:
   capturing an image stream of a patient using one or more cameras of an originating patient telehealth device;
   obtaining patient information including medical information of the patient from medical sensors connected to the telehealth device at the patient's location, the patient information including private information of the patient stored on the telehealth device;
   combining, at the originating patient telehealth device using a video display manager executing on the originating patient telehealth device, the patient image stream and the patient information into a single combined video stream, the video display manager layering the patient information onto the patient image stream to generate the single combined video stream having the patient information and the patient image stream combined together on the single combined video stream;
   using a video call to send the single combined video stream to a remote clinician device over a communication network;
   receiving, at the originating patient telehealth device, text or voice messages from the remote clinician device via the same video call;
   using text parser software of a remote manager executing on the originating patient telehealth device to extract commands from the text or voice messages received from the remote clinician device; and
   using system management software executing on the originating patient telehealth device to control the operation of the video display manager in accordance with the commands extracted from the text or voice messages received from the remote clinician device.

2. The method of claim 1 wherein the medical sensors connected to the telehealth device at the patient's location are from the group consisting of: a pulse oximeter, a blood pressure sensor, a stethoscope, an otoscope, and a thermometer.

3. The method of claim 1 wherein the remote clinician device is from the group consisting of: a mobile device, a cellular telephone, a tablet, and a personal computer.

4. The method of claim 1 wherein the patient information and the patient image stream are visually overlaid on the single combined video stream.

5. The method of claim 1 wherein the video call is facilitated using an application for transmitting and receiving text, voice, images, and video data.

6. The method of claim 5 wherein the application is from the group consisting of: Zoom™ and WhatsApp™.

7. The method of claim 1 wherein the same video call is used for both transmission of the single combined video stream to the remote clinician device over the communication network and for receipt of the text or voice messages from the remote clinician device over the communication network.

8. The method of claim 1 wherein controlling the operation of the video display manager in accordance with the commands extracted from the text or voice messages received from the remote clinician device further includes combining the patient image stream and the patient information into the single combined video stream, which conforms to the commands extracted from the text or voice messages received from the remote clinician device.

9. The method of claim 1 further including applying voice recognition to the voice messages received from the remote clinician device to identify the commands.

10. The method of claim 1 wherein controlling the operation of the video display manager in accordance with the commands extracted from the text or voice messages received from the remote clinician device further includes combining medical sensor data into the single combined video stream as specified by the commands extracted from the text or voice messages received from the remote clinician device.

11. A telehealth device for remotely treating a patient and configured to send both patient video and patient information through a single combined video stream over a communication network to a remote clinician device, the telehealth device comprising:
- a communication interface for relaying a single combined video stream between a remote clinician device of a medical practitioner and the telehealth device used by a patient over a communication network;
- one or more cameras for capturing an image stream of the patient;
- one or more medical sensors connected to the telehealth device at the patient's location;
- a memory; and
- a processor configured to:
  - receive the image stream of the patient from the one or more cameras;
  - obtain patient information including medical information of the patient from the one or more medical sensors, the patient information including private information of the patient stored on the telehealth device;
  - combine, at the telehealth device using a video display manager executing on the telehealth device, the patient image stream and the patient information into the single combined video stream, the video display manager layering the patient information onto the patient image stream to generate the single combined video stream having the patient information and the patient image stream combined together on the single combined video stream;
  - use a video call to send the single combined video stream to the remote clinician device over the communication network;
  - receive, at the telehealth device, text or voice messages from the remote clinician device via the same video call;
  - use text parser software of a remote manager executing on the telehealth device to extract commands from the text or voice messages received from the remote clinician device; and
  - use system management software executing on the telehealth device to control the operation of the video display manager in accordance with the commands extracted from the text or voice messages received from the remote clinician device.

12. The telehealth device of claim 11 wherein the one or more medical sensors connected to the telehealth device at the patient's location are from the group consisting of: a pulse oximeter, a blood pressure sensor, a stethoscope, an otoscope, and a thermometer.

13. The telehealth device of claim 11 wherein the remote clinician device is from the group consisting of: a mobile device, a cellular telephone, a tablet, and a personal computer.

14. The telehealth device of claim 11 wherein the patient information and the patient image stream are visually overlaid on the single combined video stream.

15. The telehealth device of claim 11 wherein the video call is facilitated using an application for transmitting and receiving text, voice, images, and video data.

16. The telehealth device of claim 15 wherein the application is from the group consisting of: Zoom™ and WhatsApp™.

17. The telehealth device of claim 11 wherein the same video call is used for both transmission of the single combined video stream to the remote clinician device over the communication network and for receipt of the text or voice messages from the remote clinician device over the communication network.

18. The telehealth device of claim 11 wherein controlling the operation of the video display manager in accordance with the commands extracted from the text or voice messages received from the remote clinician device further includes combining the patient image stream and the patient information into the single combined video stream, which conforms to the commands extracted from the text or voice messages received from the remote clinician device.

19. The telehealth device of claim 11 further including applying voice recognition to the voice messages received from the remote clinician device to identify the commands.

20. The telehealth device of claim 11 wherein controlling the operation of the video display manager in accordance with the commands extracted from the text or voice messages received from the remote clinician device is further configured to combine medical sensor data into the single combined video stream as specified by the commands extracted from the text or voice messages received from the remote clinician device.

* * * * *